United States Patent [19]
Schwartz et al.

[11] Patent Number: 4,473,458
[45] Date of Patent: Sep. 25, 1984

[54] ION MEASURING DEVICE WITH SELF-CONTAINED STORAGE OF STANDARDIZING SOLUTION

[75] Inventors: Howard Schwartz, Chappaqua, N.Y.; Gabor B. Levy, Westport, Conn.

[73] Assignee: Instrument Technology Incorporated, Chappaqua, N.Y.

[21] Appl. No.: 527,855

[22] Filed: Aug. 30, 1983

[51] Int. Cl.$^3$ ............................................. G01N 27/30
[52] U.S. Cl. ...................................... 204/433; 73/1 R; 204/416; 324/438
[58] Field of Search ......................... 204/433, 401, 416; 324/438; 73/1 R

[56] References Cited

U.S. PATENT DOCUMENTS 3,625,850 12/1971 Arrington ..................... 204/416 X
4,151,255 4/1979 Capuano et al. ................ 204/433 X
4,260,950 4/1981 Hadden et al. ...................... 324/438

Primary Examiner—G. L. Kaplan
Attorney, Agent, or Firm—John F. Ohlandt

[57] ABSTRACT

An ion measuring device (pH meter) is adapted to store and discharge standardizing solution, as well as to provide measurements of the hydrogen or other ion concentrations of unknown samples; the device including a working electrode of known construction and a reference electrode adjacent to the working electrode; and further including at least one storage reservoir for containing a standardizing solution, and a measuring or standardizing chamber located at the lower end of the reservoir with means, preferably in the form of a valve, for permitting communication between the reservoir and standardizing chamber such that standardization and calibration can be carried out.

16 Claims, 8 Drawing Figures

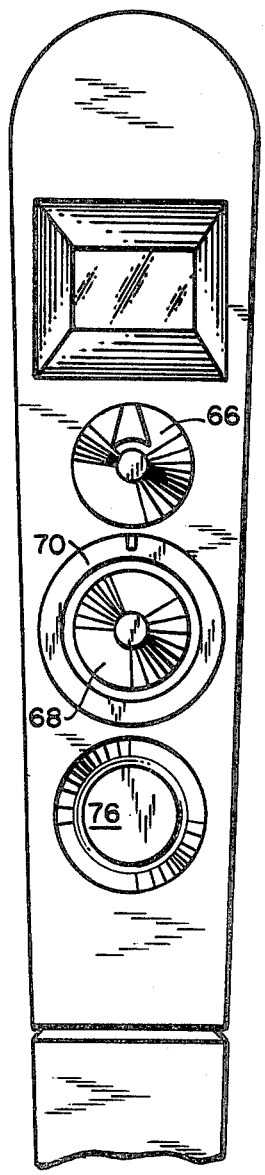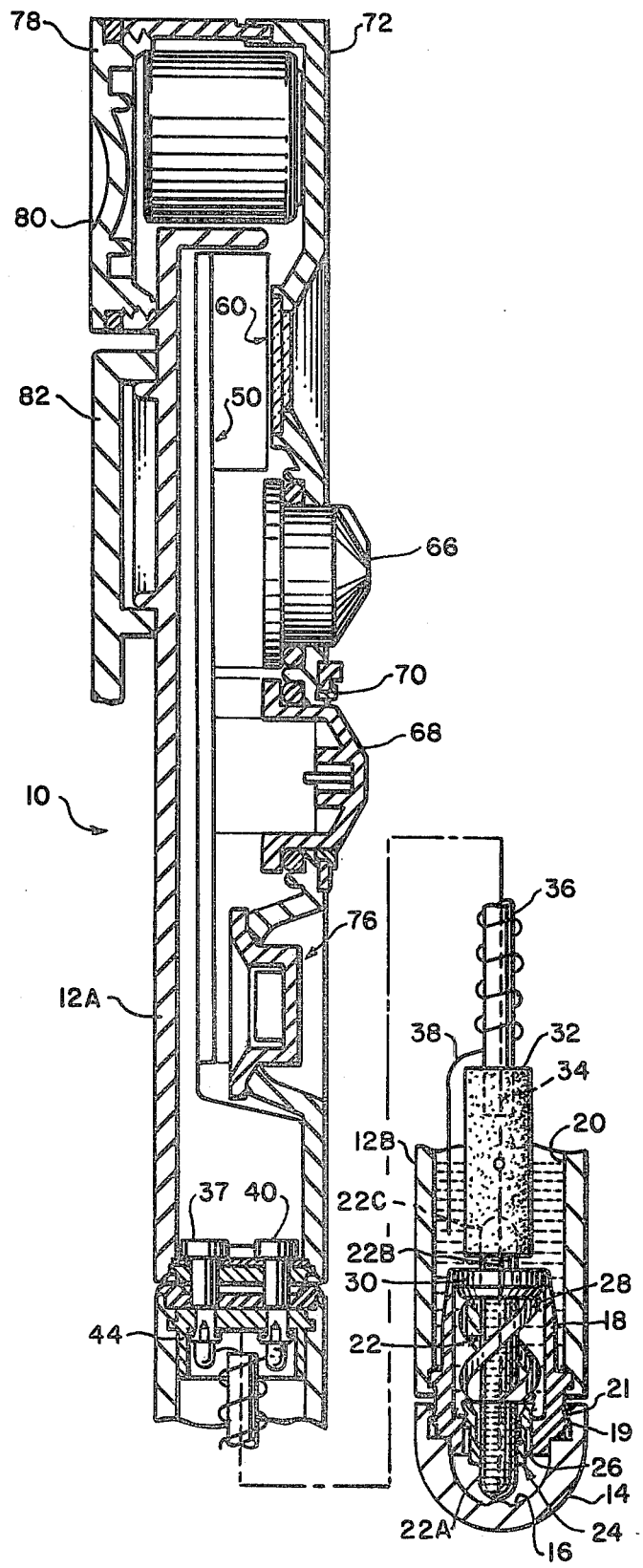

FIG. 5
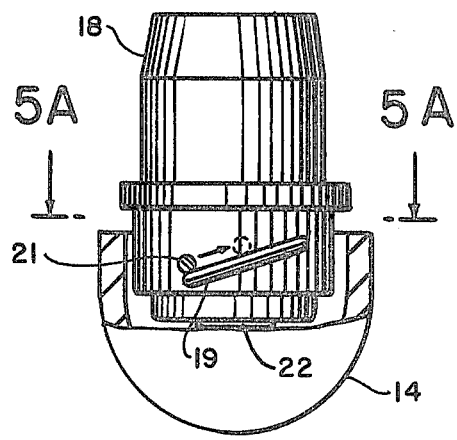
FIG. 5A
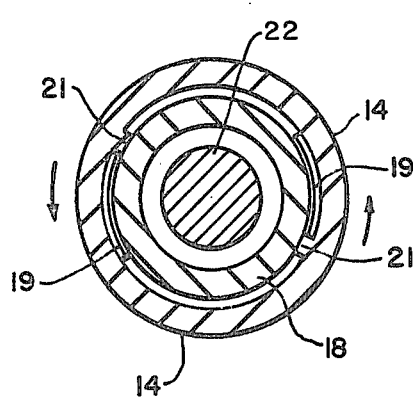
FIG. 5B
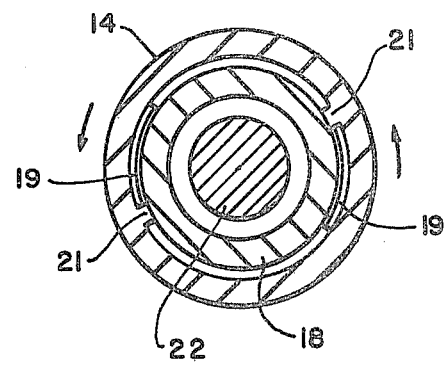
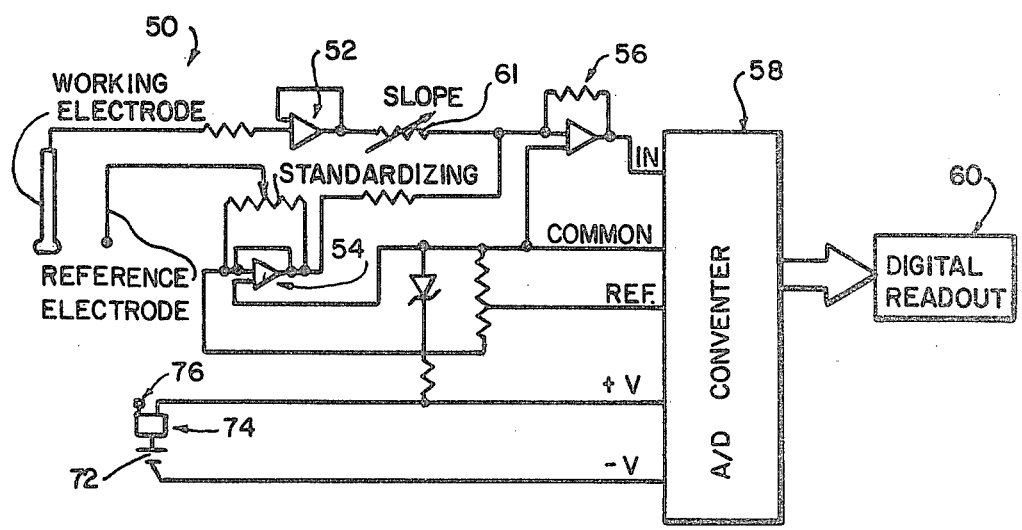
FIG. 6

ION MEASURING DEVICE WITH SELF-CONTAINED STORAGE OF STANDARDIZING SOLUTION

BACKGROUND OF THE INVENTION

1. Field of the Invention

This invention relates to the determination of the concentration of ions in solution and, more particularly, to such determination by potentiometric means.

The potentiometric determination of the electrochemical activity of ions in solution is a technique which originated almost a century ago. The first practical application was that of the measurement of hydrogen ions or pH as a measure of acidity, pH being the negative logarithm of hydrogen ion activity. Such an application is still the most widespread one, although more recently several other cations (e.g. sodium, potassium, calcium) and some anions (fluoride, chloride) are also routinely measured today by this technique.

In all of the above noted applications, two electrodes are immersed into the solution to be tested and they are connected to a high impedance voltmeter. The latter measures the potential developed by the working electrode which is selectively sensitive to the ion to be measured. This working electrode potential is measured against the potential of the reference electrode, which is a constant potential. Effectively, then what is measured is the potential difference developed by a voltaic cell, which is a function of the pH of the solution being tested. Accordingly, the pH can be determined to a high degree of accuracy if the potential difference of the cell can be measured accurately.

As to the working electrode, per se, its most important element is an ion-sensitive membrane which, in the case of pH measurement, is a glass of specific composition (see, for example, M. Cremer, Z. Biol., 47, 562 (1906); F. Haber and Z. Klemensiewicz, Z. Phys. Chem.67, 385 (1909). Because it is impractical to make an electrical connection directly to the inner glass surface, an auxiliary electrochemical cell is set up and connected to the potentiometer. Such cell conventionally consists of a silver wire coated with silver chloride. The working electrode is then filled with a solution which has an ion concentration close to the central concentration value of the ions to be measured, and which also contains chloride ions to set up a potential with the silver chloride. The working electrode, therefore, conforms to the Nernst equation:

$$E = E_o + \frac{RT}{nF} \cdot \log \frac{a}{a_s}$$

where E is the potential measured, R is the universal gas constant, F is the Faraday constant: 96,500 coulombs, T is temperature, n is the valence of the ion, $E_o$ is the standard potential, and $a_s$ the activity of a standard or reference solution, and a is the activity of the ion to be measured.

In practice then, the two electrodes are immersed in a standard solution of known activity or concentration, and the instrument is set to read this value. On the other hand, when the electrodes are immersed into an unknown solution, the potential E is a direct measure of the unknown activity according to this logarithmic relationship. The only other concern is the slope, which changes with temperature and may also fall short of the theoretical "Nernstian" behavior. Consequently, in practice, potentiometric instruments are provided with a "standardizing control" which provides a set point, and a "calibration control" which allows a change in slope. However, because the linearity of the measurements is close to perfect, a one or two point calibration suffices.

The reference electrode is similar to the inner part of the working electrode in that it contains, typically, a silver or silver chloride element surrounded by a solution containing chloride ions. Thus, this electrode has a constant potential. Another requirement for the pH measuring device is that the reference electrode must be electrolytically connected to the solution to be tested, that is, either the unknown sample or a standardizing solution, but without significant mixing of the inner contents of the reference electrode and the sample solution. This is usually achieved by means of a porous plug acting as a so called "electrochemical junction".

Over the last fifty years, a very large variety of instruments have been designed and produced to measure ion concentration and particularly to measure pH. Almost all of these instruments follow the same basic principles and the variations therein mostly relate to convenience and ease of manufacturing, or to new transducers responding to various ions not measured theretofore.

For special background material which will place the present invention in proper context, reference may be made to U.S. Pat. No. 2,058,761 and to U.S. Pat. No. 3,753,084. In the former patent, which dates to the 1930's, an apparatus is described for testing acidity whose main feature apparently relates to the provision of a potential indicating device of extreme sensitivity resulting from the ability to measure the potential of a high resistance circuit of a voltaic cell in an electrochemical environment. In such apparatus, one of the electrodes consists of a thin-wall glass bulb containing a solution of hydrochloric acid and quinhydrone of known characteristics; whereas the other electrode consists of a tube containing a solution of potassium chloride and mercurous chloride (calomel), the construction of that tube being such as to permit contact between the solution of potassium chloride and calomel within the tube and the solution to be tested. U.S. Pat. No. 2,058,761 proposes the substitution for a delicate galvanometer, previously considered necessary, a simple and mechanically rugged milliameter in combination with a specially designed vacuum tube amplifier.

The latter patent noted above, that is, Wirz U.S. Pat. No. 3,753,084 discloses an apparatus for the rapid electrometric determination of ionic activities, especially the pH value. According to the invention described therein, there is provided as the sensor an electrode measuring chain possessing measuring and reference electrode means. One of the principal features described therein is a storage vessel which is provided for the measuring chain, the storage vessel containing an activation solution to maintain said measuring chain under the influence of the solution when the measuring chain is not being employed for the purpose of obtaining the ion concentration of an unknown. The activation solution mentioned in that patent can have the same chemical composition as the conductive electrolyte in which the reference electrode wire is immersed, such conductive electrolyte containing stabilization additives and the like.

In any event, regardless of the particular merits of the devices already developed in the prior art and the particular apparatus described in the specific references cited above, none of the previous developments make it possible to take full advantage of state-of-the-art electronics and to avoid difficulties involved in periodically adjusting the instrument, i.e. of utilizing standardizing and calibration controls so that assurance is gained of accurate readings of particular electrochemical activities for given ion concentrations.

Accordingly, it is a primary object of the present invention to eliminate the need for an operator to carry at least one standardizing solution with a pH measuring device so as to enable him to periodically adjust the device to take care of variations in set point which is bound to occur with use.

A further object of the present invention is to provide a truly portable potentiometric instrument which is self-contained and no larger than a typical marking pen. The practical importance of such a device is great because a large proportion of important measurements of this character must be made by semi-skilled operators in locations removed from a chemical laboratory. The present device allows this to be done in a manner akin to temperature measurements with a simple thermometer.

The above noted primary object of the invention is fulfilled by the inclusion of a reservoir of standardizing solution as part of the combination of two electrodes which are essential to the operation of the measuring device. In other words, rather than carrying a separate container of standardizing solution, the container or reservoir of such solution is built into the measuring device. Preferably, the way this is done is to have the reservoir solution correspond with the reference solution. Thus the reference solution can consist of the requisite chloride, such as sodium chloride, along with buffering agents as required; furthermore, a means is provided at the lower end of the housing for the two electrodes so as to be able selectively to permit fluid to flow from the reservoir into the standardizing chamber so as to surround the lower end of the working electrode when standardization is desired. This means preferably takes the form of a valve, which also serves as the electrochemical junction of the reference electrode in the preferred form.

Accordingly, broadly stated, the invention resides in an ion measuring device adapted to store and discharge standardizing solution comprising a housing; a working electrode, including an electrode wire immersed in a solution contained within a sealed, ion-selective envelope, disposed in said housing; a storage reservoir adjacent said envelope containing standardizing solution; a reference electrode, including an electrochemical junction and an electrode wire immersed in a reference solution, disposed in said housing; a standardizing chamber defined at the lower end of said housing and surrounding at least a portion of said working electrode; means at the lower end of said housing for selectively providing communication between said standardizing chamber and said reservoir, such that fluid flows from said reservoir into said standardizing chamber, thereby to wet the ion-sensitive surface of said working electrode and to wet the reference electrode electrochemical junction when said communication means is activated for standardization purposes.

Other and further objects, advantages and features of the present invention will be understood by reference to the following specification in conjunction with the annexed drawing, wherein like parts have been given like numbers.

BRIEF DESCRIPTION OF THE DRAWING

FIG. 3 is a front elevational fragmentary view of the upper portion or part of the ion measuring device.

FIG. 4 is an enlarged side sectional view of the device.

FIG. 5 is a view of the lower portion of the housing, particularly illustrating the cap defining the standardizing chamber.

FIGS. 5A and 5B are cross sections of FIG. 5 showing the cap in two different positions.

FIG. 6 is a block diagram of the electronics involved in the device of the present invention.

DESCRIPTION OF PREFERRED EMBODIMENT

Figure 1:
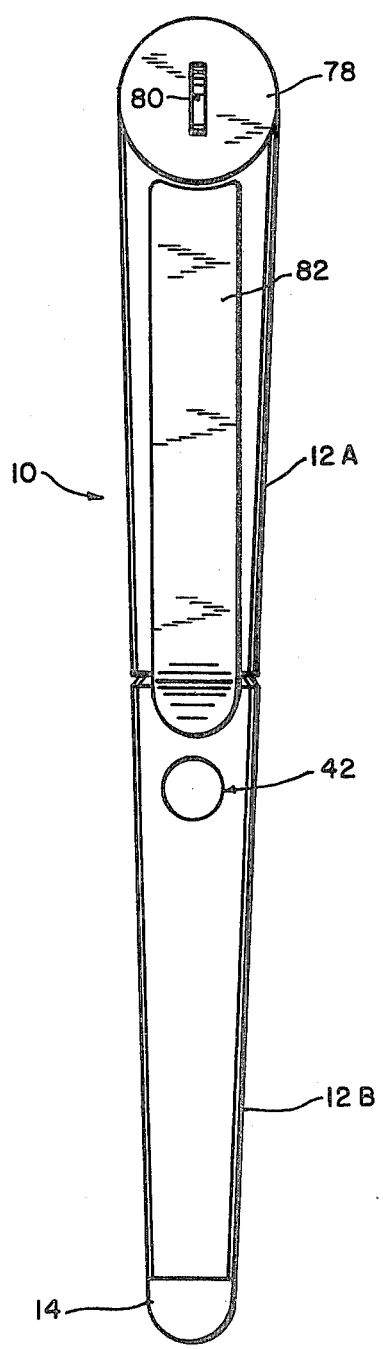
FIG. 1 is a rear elevational view of the ion measuring device in accordance with one embodiment of the present invention.
Figure 2:
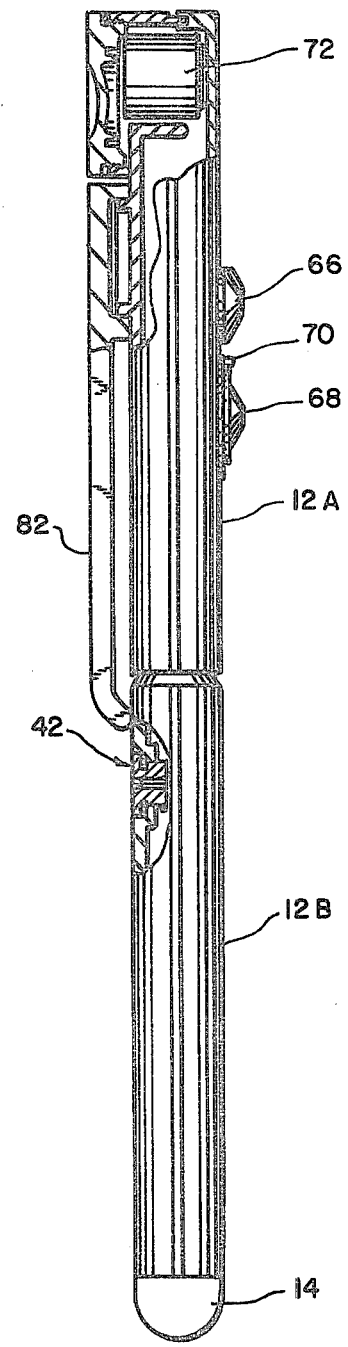
FIG. 2 is a side elevational view partly broken away in section to show internal parts.

The preferred embodiment of the ion measuring device of the present invention is shown in FIGS. 1–6. The device or instrument 10 is an integral or self-contained portable device having three major constituents; namely an electronic module, an electrode assembly and a standardizing chamber, to be described. The housing for the measuring device 10 is divided into two major portions or parts: part 12A houses the electronics components, and part 12B houses the electrode components or assembly. A movable cap-like member 14 is attached at the bottom of lower housing part 12B. A standardizing chamber 16 is defined at the interior of member 14, thus comprising a unique feature of the present invention as already noted. Also provided is a barrel 18, fixedly held at the interior of lower housing part 12B. The movable member 14 is engaged at the protruding lower end of this barrel by the arrangement of pins 19 and threads 21, whereby upward movement of member 14 can be effected when it is rotated.

A standardizing solution in the preferred embodiment illustrated is contained in a chamber 20 forming a reservoir at the interior of housing part 12B. Since the barrel 18 is open at its top, the standardizing solution is also contained within the barrel 18 so as to be poised for discharge into standardizing chamber 16. The working electrode 22 is carried or supported on a valve member 24, which seats in a tapered bore 26 of the barrel 18, the valve member being appropriately tapered. The valve member 24 is biased into its closed position by means of a spring 28 disposed within the barrel 18. The upper end of such spring is restrained by a stationary ring 30 captured or held at the interior of barrel 18.

In operation, assuming that the movable member of cap 14 is attached, clockwise rotation of this cap causes lifting of valve 24 since the interior thereof then engages the lower end 22A of the working electrode 22. Consequently, a small amount of the standardizing solution held in the chamber 20 is discharged. As will be appreciated from FIG. 5, slight counterclockwise twisting of the cap 14 permits the valve to return to the closed position, whereas extended twisting enables removal of the cap. In this manner, the device or instrument can be standardized at any time before measuring an unknown sample, and the standardizing solution that was discharged into the cap can be thrown away.

The working electrode 22 includes an electrode wire 22B and envelope 22C. Contained within the glass envelope 22C is a suitable solution which, in the particular embodiment under consideration, can be a standardizing solution identical to that described below.

It will be seen that the upper end of the working electrode wire 22B is embedded in a silicone mold 32, a further wire 34 being solder-connected to the electrode wire 22B. The wire 34 is contained in a waterproof cable 36. Electrical connection of the wire 34 to the electronic system included as part of device 10 is accomplished by means of an upper connector 37. The circuit is completed by connection of a silver chloride wire 38, which is wrapped around the cable 36 for shielding, such wire being connected to another upper connector 40.

It is to be noted that the connectors 37 and 40 serve not only as inputs to the electronic system of the ion measuring device per se, but they also function as locking devices. Accordingly, by the use of such connectors, the electrodes become replaceable and the two parts 12A and 12B of the housing are readily separable. As will be seen, especially in FIG. 4, the chamber 20 contains the required standardizing solution which is to be discharged whenever adjustment must be made in the offset so that the electronic system will correctly read the ion concentration of an unknown sample.

In the embodiment seen in the figures, the standardizing solution corresponds with the reference solution. Thus, the dischargeable standardizing solution is the solution in which the reference electrode 38 is immersed. The standardizing solution can be typically composed of a buffer containing chloride ions and saturated with silver chloride, as well as a small amount of disinfectant. The preferred composition is:

| | |
|---|---|
| $NaH_2PO_4.H_2O$ | 7.77 g |
| $K_2HPO_4$ | 17.05 g |
| NaCl | 2.92 g |
| Thymol | 0.05 g | in 500 ml $H_2O$, saturated with AgCl.

As noted previously, this same composition can also serve as the solution contained in the glass envelope 22C of the working electrode 22. In order to fill the chamber 20 of the device with the standardizing solution, a filling enclosure 42 is provided at the rear of the housing. This closure contains a gas permeable, but liquid-tight membrane for pressure equalization.

The upper part 12A of the housing contains all of the electronics and is separated from the lower part 12B, which is the liquid-containing compartment, by means of a watertight closure 44.

Referring now to the block diagram of FIG. 6, there is shown a hybrid miniaturized circuit 50 which enables the digital read-out resulting from potentials developed by the already described working and reference electrodes of the ion-measuring device 10. Suitable wiring, not seen in FIG. 4, connects the working and reference electrodes to the electronic module contained in the upper housing part 12A. The circuit 50 includes a number of operational amplifiers 52, 54 and 56 for purposes well understood in the art, such that the resultant analog signals therefrom are transmitted to an A to D converter 58, whereby the output can furnish a digital read-out by means of a typical liquid crystal display 60, such display being viewable on the front face of the device 10 as seen in FIG. 4.

In order to provide the requisite standardizing, i.e., offset adjustment, and slope adjustment, potentiometers 62 and 64 respectively are employed for these purposes, being controlled from the front face of the device 10 by the knobs 66 and 68 respectively.

It will be understood that the digital readout display 60 reads directly in pH units over the full range of values: 0 to 14. It is to be noted that the calibration of slope control includes an annular temperature scale 70 surrounding the knob 68 so as to permit temperature correction according to the Nernst equation.

A single three-volt replaceable battery 72 is housed in the upper portion of housing part 12A. Because CMOS electronics are used throughout, the battery life is long, typically three to twelve months. In order to enhance battery life, a solid state ON-OFF switch 74 is incorporated on the board for the circuit 50. Such switch is activated by pushbuttons 76 on the face of the device. The switching is such that when the switch is kept depressed, the digital readout will display the battery voltage.

A removable battery compartment cover 78 having a coin slot 80 is provided. Also, for convenience and ease of use, a clip 82 is provided on the rear face of the device. The entire electrode section, that is, the housing part 12B, can be detached for replacement of the electrode assembly by simply pressing parts 12A and 12B together and twisting.

It will be appreciated in the operation of the device of the present invention, that, as explained, the cap 14 can be rotated or twisted to produce activation of the valve 24 so as to discharge solution from the storage reservoir, which, in the preferred embodiment, corresponds with the reference electrode. However, when an unknown sample is to be measured or tested for determining ion concentration value, the cap 14 is entirely removed. In this case, the unknown sample wets the thin bulbous portion 22A at the end of the working electrode 22 and conduction is completed by reason of the electrochemical junction provided by the movable valve member 24. In other words, there is always a slight wetting of the tapered surfaces of the valve member and the tapered seat 26. When standardizing, the same wetting occurs of the portion 22A and the electrochemical junction defined by the valve member 24 cooperating with the tapered seat 26.

It will be understood that other embodiments of the ion detection device of the invention can be provided. Instead of the preferred embodiment, an alternate embodiment would include, in place of the illustrated reference electrode, a reference electrode defined, for example, by another envelope surrounding the envelope 22C and containing a reference solution which could differ somewhat from the standardizing solution already described. Both electrodes could be mounted together as a unit on the movable valve member 24, and a porous plug or the like could be used on a lowermost portion of such reference electrode envelope. In that case, the standardizing solution could be contained in a chamber much like chamber 20 and could be discharged by activation of the valve member 24. In this modified construction, the valve member 24 serves only as a means of discharging and does not serve as in the preferred embodiment to produce the electrochemical junction required.

While there have been shown and described what are considered at present to be the preferred embodiments of the present invention, it will be appreciated by those skilled in the art that modifications of such embodiments may be made. It is therefore desired that the invention not be limited to these embodiments, and it is intended to cover in the appended claims all such modifications as fall within the true spirit and scope of the invention.

What is claimed is:

1. An ion measuring device adapted to store and discharge standardizing solution comprising:
    an elongate, electrode housing;
    a working electrode, including an electrode element immersed in a solution contained within a sealed, ion-selective envelope, disposed in said housing;
    a storage reservoir, within said housing and surrounding said envelope, for containing standardizing solution;
    a reference electrode disposed in said housing, said electrode including an electro-chemical junction and an electrode element immersed in a reference solution;
    a standardizing chamber defined at the lower end of said housing and surrounding at least a portion of said working electrode;
    means at the lower end of said housing for selectively providing communication between said standardizing chamber and said reservoir, such that fluid flows from said reservoir into said standardizing chamber, thereby to wet the ion-sensitive surface of said working electrode and to wet the reference electrode junction when said communication means is activated for standardization purposes.

2. A device as defined in claim 1, in which said communication means is a valve.

3. A device as defined in claim 1, in which said reference electrode is contained within a second envelope.

4. A device as defined in claim 1, in which said working electrode is supported on said communication means and extends into said standardizing chamber.

5. An ion measuring device adapted to store and discharge standardizing solution comprising:
    an elongate electrode housing;
    a working electrode, including an electrode element immersed in a solution contained within a sealed, ion-selective envelope, disposed in said housing;
    a storage reservoir, within said housing and surrounding said envelope, for containing standardizing solution;
    a reference electrode, including an electro-chemical junction and an electrode element immersed in a reference solution, disposed in said housing;
    a standardizing chamber defined at the lower end of said housing and surrounding at least a portion of said working electrode;
    means at the lower end of said housing for selectively providing communication between said standardizing chamber and said reservoir, such that fluid flows from said reservoir into said standardizing chamber, thereby to wet the ion-sensitive surface of said working electrode and to wet the reference electrode junction when said communication means is activated for standardization purposes;
    and electronic means for measuring the difference in potential between said working electrode and said reference electrode to determine the ion concentration of a fluid wetting both electrodes.

6. A device as defined in claim 5, in which said communication means is a valve.

7. A device as defined in claim 5, in which said reference electrode is contained within a second envelope.

8. A device as defined in claim 5, in which said working electrode is supported on said communication means and extends into said standardizing chamber.

9. A device as defined in claim 5, further comprising potentiometric means for adjusting the set point of said device when standardizing solution is present in said chamber.

10. A device as defined in claim 5, further comprising means for displaying the ion concentration of said fluid.

11. An ion measuring device adapted to store and discharge standardizing solution comprising:
    a housing;
    a working electrode, including an electrode element immersed in a solution contained within a sealed, ion-selective envelope, disposed in said housing;
    a storage reservoir, adjacent said envelope for containing standardizing solution;
    a reference electrode disposed in said housing, said electrode including an electro-chemical junction and an electrode element immersed in a reference solution;
    in which said reservoir is defined by the reference electrode, and said reference solution is said standardizing solution;
    a standardizing chamber defined at the lower end of said housing and surrounding at least a portion of said working electrode;
    means at the lower end of said housing for selectively providing communication between said standardizing chamber and said reservoir, such that fluid flows from said reservoir into said standardizing chamber, thereby to wet the ion-sensitive surface of said working electrode and to wet the reference electrode junction when said communication means is activated for standardization purposes.

12. A device as defined in claim 11, in which said communication means is a valve which also functions as said electrochemical junction between the solution in said standardizing chamber and said reservoir.

13. An ion measuring device adapted to store and discharge standardizing solution comprising:
    a housing;
    a working electrode, including an electrode element immersed in a solution contained within a sealed, ion-selective envelope, disposed in said housing;
    a storage reservoir adjacent said envelope for containing standardizing solution;
    a reference electrode, including an electro-chemical junction and an electrode element immersed in a reference solution, disposed in said housing;
    in which said reservoir is defined by the reference electrode, and said reference solution is said standardizing solution;
    a standardizing chamber defined at the lower end of said housing and surrounding at least a portion of said working electrode;
    means at the lower end of said housing for selectively providing communication between said standardizing chamber and said reservoir, such that fluid flows from said reservoir into said standardizing chamber, thereby to wet the ion-sensitive surface of said working electrode and to wet the reference electrode junction when said communication means is activated for standardization purposes;
    and electronic means for measuring the difference in potential between said working electrode and said reference electrode to determine the ion concentration of a fluid wetting both electrodes.

14. A device as defined in claim 13, in which said communication means is a valve which also functions as said electrochemical junction between the solution in said standardizing chamber and said reservoir.

15. An ion measuring device adapted to store and discharge standardizing solution comprising:
a housing;
a working electrode, including an electrode element immersed in a solution contained within a sealed, ion-selective envelope, disposed in said housing;
a storage reservoir, adjacent said envelope for containing standardizing solution;
a reference electrode disposed in said housing, said electrode including an electro-chemical junction and an electrode element immersed in a reference solution;
a standardizing chamber defined at the lower end of said housing and surrounding at least a portion of said working electrode;
in which said standardizing chamber is defined by a rotatable member removably attached to the lower end of said housing;
means at the lower end of said housing for selectively providing communication between said standardizing chamber and said reservoir, such that fluid flows from said reservoir into said standardizing chamber, thereby to wet the ion-sensitive surface of said working electrode and to wet the reference electrode junction when said communication means is activated for standardization purposes.

16. An ion measuring device adapted to store and discharge standardizing solution comprising:
a housing;
a working electrode, including an electrode element immersed in a solution contained within a sealed, ion-selective envelope, disposed in said housing;
a storage reservoir adjacent said envelope for containing standardizing solution;
a reference electrode including an electro-chemical junction and an electrode element immersed in a reference solution, disposed in said housing;
a standardizing chamber defined at the lower end of said housing and surrounding at least a portion of said working electrode;
in which said standardizing chamber is defined by a rotatable member removably attached to the lower end of said housing;
means at the lower end of said housing for selectively providing communication between said standardizing chamber and said reservoir, such that fluid flows from said reservoir into said standardizing chamber, thereby to wet the ion-sensitive surface of said working electrode and to wet the reference electrode junction when said communication means is activated for standardization purposes;
and electronic means for measuring the difference in potential between said working electrode and said reference electrode to determine the ion concentration of a fluid wetting both electrodes.

* * * * *